United States Patent [19]

Stähle et al.

[11] 4,409,235

[45] Oct. 11, 1983

[54] SUBSTITUTED 7-(2,6-DIBROMO-4-METHYL-PHENYL)-2,3-DIHYDRO-IMIDAZO[1,2-A]IMIDAZOLES, COMPOSITIONS AND USE

[75] Inventors: Helmut Stähle; Herbert Köppe; Werner Kummer, all of Ingelheim am Rhein, Fed. Rep. of Germany; Walter Kobinger, Vienna, Austria; Christian Lillie, Vienna, Austria; Ludwig Pichler, Vienna, Austria

[73] Assignee: C. H. Boehringer Sohn, Ingelheim am Rhein, Fed. Rep. of Germany

[21] Appl. No.: 404,538

[22] Filed: Aug. 2, 1982

Related U.S. Application Data

[63] Continuation of Ser. No. 317,014, Nov. 2, 1981, abandoned.

[30] Foreign Application Priority Data

Nov. 12, 1980 [DE] Fed. Rep. of Germany ....... 3042636

[51] Int. Cl.$^3$ .................... A61K 31/415; C07D 487/04

[52] U.S. Cl. ................................ 424/273 R; 548/324

[58] Field of Search ..................... 548/324; 424/273 R

[56] References Cited

U.S. PATENT DOCUMENTS 4,210,659 7/1980 Stähle et al. ........................ 548/324

FOREIGN PATENT DOCUMENTS 2827617 1/1980 Fed. Rep. of Germany .

*Primary Examiner*—Robert W. Ramsuer
*Attorney, Agent, or Firm*—Hammond & Littell, Weissenberger & Muserlian

[57] ABSTRACT

Compounds of the formula

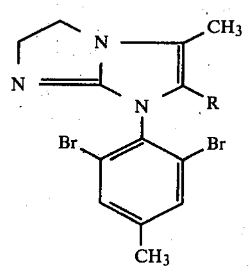

wherein R is hydrogen or methyl, and non-toxic, pharmacologically acceptable acid addition salts thereof. The compounds as well as their salts are useful as bradycardiacs.

5 Claims, No Drawings

SUBSTITUTED 7-(2,6-DIBROMO-4-METHYL-PHENYL)-2,3-DIHYDRO-IMIDAZO[1,2-A]IMIDAZOLES, COMPOSITIONS AND USE

This is a continuation of copending application Ser. No. 317,014, filed Nov. 2, 1981, now abandoned.

This invention relates to novel substituted 7-(2,6-dibromo-4-methyl-phenyl)-2,3-dihydro-imidazo[1,2-a]imidazoles and non-toxic acid addition salts thereof, to methods of preparing these compounds, to pharmaceutical compositions containing them as active ingredients, and to a method of using them as bradycardiacs.

More particularly, the present invention relates to a novel class of compounds represented by the formula

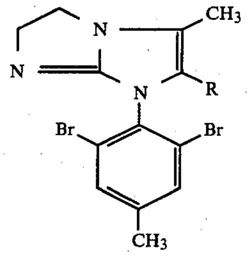

(I)

wherein R is hydrogen or methyl, and non-toxic, pharmacologically acceptable acid addition salts thereof.

The compounds embraced by formula I may be prepared by various methods involving known principles of chemical synthesis, among which the following have proved to be particularly convenient and efficient.

Method A

By reacting 2-(2,6-dibromo-4-methylphenyl-imino)-imidazolidine of the formula

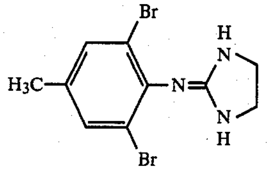

(II)

with an oxo compound of the formula

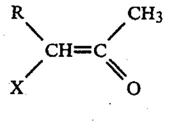

(III)

wherein

R has the same meanings as in formula I, and

X is chlorine, bromine or iodine.

The reaction is advantageously carried out by heating the reactants, preferably in the presence of a polar or non-polar organic solvent, to a temperature between about 60°-180° C. The particular reaction conditions depend to a large extent upon the reactivity of the reactants. If desired or necessary, the reaction may be performed in the presence of an acid-binding agent such as triethylamine.

Method B

By cyclizing a 2-[N-propargyl-N-(2,6-dibromo-4-methylphenyl)-amino]-2-imidazoline of the formula

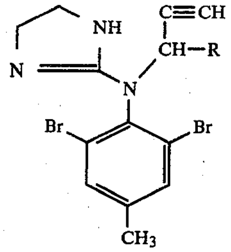

(IV)

wherein R has the same meanings as in formula I.

The cyclization is effected by heating the starting compound to an elevated temperature, preferably to between 50° and 150° C., in the presence of a polar or non-polar solvent and advantageously in the presence of an organic base such as trimethylbenzyl ammonium hydroxide.

Method C

By dehydrating a 7-(2,6-dibromo-4-methylphenyl)-5-hydroxy-5-methyl-2,3,5,6-tetrahydro-imidazo[1,2-a]-imidazole of the formula

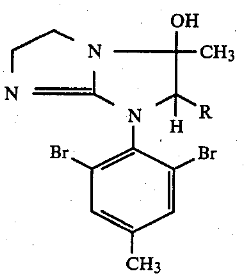

(V)

at a temperature between 60° and 180° C. and/or in the presence of a dehydrating agent. The reaction may be performed in the presence or absence of a solvent.

Method D

By reacting a 1-(2,6-dibromo-4-methylphenyl)-2-imino-4-methyl-4-imidazoline of the formula

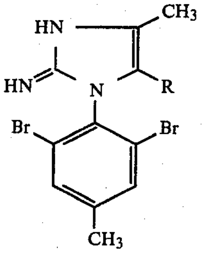

(VI)

wherein R has the same meanings as in formula I, with 1,2-dibromo ethane. The reaction is performed at elevated temperatures, preferably between 80° and 180° C., and may be carried out in the presence of a solvent, although the presence of a solvent is not required.

The starting compounds of the formula II are disclosed in Belgian Pat. No. 623,305, 687,657 and 705,944.

The compounds of the formula III are available in commerce and are described in the literature.

The starting compounds of the formula IV are disclosed in German Offenlegungsschrift No. 2,523,103.

Compounds of the formula V can be obtained by reacting 2-(2,6-dibromo-4-methylphenyl-imino)-imidazolidine of the formula II with a compound of the formula III at reduced temperature. Starting compounds of the formula VI are obtained by reacting N-(2,6-dibromo-4-methyl-phenyl)-guanidine of the formula

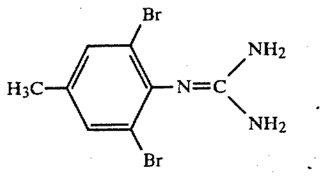

(VII)

with a compound of the formula III.

The end products of the formula I are organic bases and therefore form acid addition salts with inorganic or organic acids. Examples of non-toxic, pharmacologically acceptable acid addition salts are those formed with mineral acids such as hydrochloric acid, hydrobromic acid, hydriodic acid, hydrofluoric acid, sulfuric acid, phosphoric acid or nitric acid, or organic acids such as acetic acid, propionic acid, butyric acid, caproic acid, caprinic acid, valeric acid, oxalic acid, malonic acid, succinic acid, maleic acid, fumaric acid, lactic acid, tartaric acid, citric acid, malic acid, benzoic acid, p-hydroxy-benzoic acid, p-amino-benzoic acid, phthalic acid, cinnamic acid, salicylic acid, ascorbic acid, methanesulfonic acid, ethanephosphoric acid, 8-chloro-theophylline or the like.

The following examples illustrate the present invention and will enable others skilled in the art to understand it more completely. It should be understood, however, that the invention is not limited solely to the particular examples given below.

EXAMPLE 1

7-(2,6-Dibromo-4-methyl-phenyl)-2,3-dihydro-5-methylimidazo[1,2-a]-imidazole by method A 4.75 gm of 2-(2,6-dibromo-4-methyl-phenylimino)-imidazolidine (0.014 mol) were refluxed for 12 hours with 1.4 ml (120%) of chloroacetone in 25 ml of glycol monomethyl ether. The clear reaction mixture was evaporated to dryness in vacuo, and the light brown oily residue was dissolved in 1 N HCl. The hydrochloric acid solution was adjusted to pH 7 with dilute NaOH and, starting from this pH-value, it was fractionally extracted with ether at increasing pH values (NaOH). The uniform ether extracts (checked by thin-layer chromatography) were combined, dried over $MgSO_4$ and evaporated in vacuo. The novel imidazo[1,2-a]imidazole of the formula

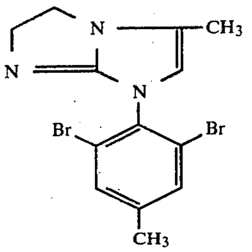

was initially obtained as an oil and then crystallized out after a short time. Yield: 0.95 gm, corresponding to 17.9% of theory. Melting point: 144°-146° C.

$C_{13}H_{13}Br_2N_3$ (371.1)

Found: C 42.05%; H 3.18%; Br 42.21%; N 10.90%

Calc.: C 42.08%; H 3.53%; Br 43.07%; N 11.32%.

EXAMPLE 2

7-(2,6-Dibromo-4-methyl-phenyl)-2,3-dihydro-5,6-dimethylimidazo[1,2-a]-imidazole by method A 5.0 gm (0.015 mol) of 2-(2,6-dibromo-4-methyl-phenylimino)-imidazolidine were refluxed for about 30 hours with 1.8 gm (110%) of 96% 3-chloro-2-butanone in 25 ml of glycol monomethyl ether. The reaction mixture was then evaporated to dryness in vacuo, and the oily residue was dissolved in 1 N hydrochloric acid. The hydrochloric acid solution was adjusted to a pH value of 7 with dilute NaOH and, starting from the pH value, was fractionally extracted with ether at increasing pH values (NaOH). The ether extracts which were uniform according to thin-layer chromatography were combined, dried over magnesium sulfate, and the ether was eliminated in vacuo. The residual oil crystallized out after a short time. Yield: 0.4 gm of the compound of the formula

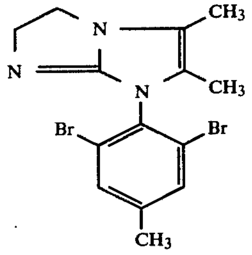

corresponding to 7% of theory. Melting point: 154°-156° C.

$C_{14}H_{15}Br_2N_3$ (385.1)

Found: C 43.80%; H 3.89%; Br 41.68%; N 10.9%

Calc.: C 43.66%; H 3.93%; Br 41.50%; N 10.9%.

The compounds of the present invention, that is, those embraced by formula I above and their non-toxic, pharmacologically acceptable acid addition salts, have useful pharmacodynamic properties. More particularly, they exhibit bradycardiac activity in warm-blooded animals such as rats, and are therefore useful for the treatment of coronary diseases.

The bradycardiac properties of the compounds were ascertained on spinal rats. For instance, we have found that a dose of 0.2 to 1.2 mgm/kg of the compounds lowers the heart rate of spinal rats by 150 beats per minute.

For pharmaceutical purposes the compounds of the present invention are administered to warm-blooded animals perorally, parenterally or rectally as active ingredients in customary dosage unit compositions, that is, compositions in dosage unit form consisting essentially of an inert pharmaceutical carrier and one effectiveness dosage unit of the active ingredient, such as tablets, coated pills, capsules, wafers, powders, solutions, suspensions, emulsions, syrups, suppositories and the like. One effective oral dosage unit of the compounds according to the present invention is from 0.0016 to 1.67 mgm/kg body weight, preferably 0.0083 to 0.83 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 3

Coated pills

The pill core composition is compounded from the following ingredients:

| | | |
|---|---|---|
| 7-(2,6-Dibromo-4-methyl-phenyl)-2,3-dihydro-5-methyl-imidazo-[1,2-a]imidazole | | 5 parts |
| Lactose | | 65 parts |
| Corn starch | | 130 parts |
| Sec. calcium phosphate | | 40 parts |
| Soluble starch | | 3 parts |
| Magnesium stearate | | 3 parts |
| Colloidal silicic acid | | 4 parts |
| | Total | 250 parts |

Preparation:

The active ingredient is admixed with a portion of all of the excipients, the mixture is thoroughly kneaded with an aqueous solution of the soluble starch, and the moist mass is granulated through a screen. The granulate is dried and intimately admixed with the remainder of the excipients, and the mixture is compressed into 250 mgm-pill cores which are then coated with a thin shell consisting essentially of a mixture of sugar, talcum and gum arabic. Each coated pill is an oral dosage unit composition containing 5 mgm of the active ingredient.

EXAMPLE 4

Hypodermic solution

The solution is compounded from the following ingredients:

| | | |
|---|---|---|
| 7-(2,6-Dibromo-4-methyl-phenyl)-2,3-dihydro-5-methyl-imidazo-[1,2-a]imidazole | | 1.0 parts |
| Sodium chloride | | 18.0 parts |
| Distilled water | q.s. ad | 2000.0 parts by vol. |

Preparation:

The active ingredient and the sodium chloride are dissolved in the distilled water, the solution is filtered until free from suspended particles, and the filtrate is filled into 2 cc-ampules which are subsequently sterilized and sealed. The contents of each ampule are an injectable dosage unit composition containing 1 mgm of the active ingredient.

EXAMPLE 5

Drop solution

The solution is compounded from the following ingredients:

| | | |
|---|---|---|
| 7-(2,6-Dibromo-4-methyl-phenyl)-2,3-dihydro-5,6-dimethyl-imidazo-[1,2-a]-imidazole | | 0.02 parts |
| Methyl p-hydroxy-benzoate | | 0.07 parts |
| Propyl p-hydroxy-benzoate | | 0.03 parts |
| Demineralized water | q.s. ad | 100.0 parts by vol. |

Preparation:

The active ingredient and the p-hydroxy-benzoates are dissolved in a sufficient amount of demineralized water, the solution is diluted to the indicated volume with additional demineralized water and then filtered, and the filtrate is filled with 100 cc-bottles equipped with a dropping spout. 10 ml of the contents of the bottle are an oral dosage unit composition containing 2 mgm of the active ingredient.

Any one of the other compounds embraced by formula I or a non-toxic, pharmacologically acceptable acid addition salt thereof may be substituted for the particular active ingredient in Examples 1 through 5. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

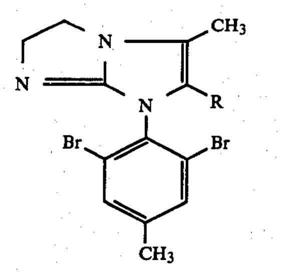

wherein R is hydrogen or methyl, or a non-toxic, pharmacologically acceptable acid addition salt thereof.

2. A compound of claim 1, which is 7-(2,6-dibromo-4-methyl-phenyl)-2,3-dihydro-5-methyl-imidazo[1,2-a]imidazole or a non-toxic, pharmacologically acceptable acid addition salt thereof.

3. A compound of claim 1, which is 7-(2,6-dibromo-4-methyl-phenyl)-2,3-dihydro-5,6-dimethyl-imidazo[1,2-a]-imidazole or a non-toxic, pharmacologically acceptable acid addition salt thereof.

4. A bradycardiac pharmaceutical composition consisting essentially of an inert pharmaceutical carrier and an effective bradycardiac amount of a compound of claim 1.

5. The method of lowering the heart rate of a warm-blooded animal in need thereof, which comprises perorally, parenterally or rectally administering to said warm-blooded animal an effective bradycardiac amount of a compound of claim 1.

* * * * *